United States Patent [19]

Hayakawa et al.

[11] Patent Number: 5,395,757
[45] Date of Patent: Mar. 7, 1995

[54] METHOD FOR THE HYDROLYSIS OF SUGAR COMPOUNDS AND REAGENT THEREFOR

[75] Inventors: Kumi Hayakawa, Kyoto; Mutsumi Sano, Otsu; Ikunoshin Kato, Uji, all of Japan

[73] Assignee: Takara Shuzo Co., Ltd., Japan

[21] Appl. No.: 879,263

[22] Filed: May 7, 1992

[30] Foreign Application Priority Data

May 15, 1991 [JP] Japan ................... 3-138563

[51] Int. Cl.$^6$ .................... C12P 19/26; C12P 19/28; C12N 9/24
[52] U.S. Cl. ................................... 435/84; 435/85; 435/95; 435/100; 435/200; 435/206; 435/207
[58] Field of Search ................... 435/85, 95, 200, 206, 435/207, 84, 100

[56] References Cited

U.S. PATENT DOCUMENTS

| | | | |
|---|---|---|---|
| 4,918,009 | 4/1990 | Nilsson | 435/73 |
| 4,990,450 | 2/1991 | Tochikura et al. | 435/200 |
| 5,041,236 | 8/1991 | Carpenter et al. | 252/174.12 |
| 5,100,778 | 3/1992 | Rademacher et al. | 435/18 |

FOREIGN PATENT DOCUMENTS 0292158  11/1988  European Pat. Off. ........ C12N 9/38

OTHER PUBLICATIONS

Iwase, et al. Bioc. Biophys. Res. Comm., 151(1), 422-428, Feb. 29, 1988.

Primary Examiner—Douglas W. Robinson
Assistant Examiner—F. C. Prats
Attorney, Agent, or Firm—Wenderoth, Lind & Ponack

[57] ABSTRACT

A method for the hydrolysis of only the lacto-N-biosidic (Gal$\beta$1-3GlcNAc$\beta$1-) linkages at the non-reducing termini of sugar compounds, characterized by the use of glycosidase that is specific for only the lacto-N-biosidic linkage in said sugar compounds. And disclosed is a reagent for use in hydrolysis of only the lacto-N-biosidic linkage at the non-reducing termini of sugar compounds.

2 Claims, 3 Drawing Sheets

METHOD FOR THE HYDROLYSIS OF SUGAR COMPOUNDS AND REAGENT THEREFOR

BACKGROUND OF THE INVENTION

1. Field of the Invention

This invention relates to a method for the hydrolysis of only the lacto-N-biosidic (Gal$\beta$1-3GlcNAc$\beta$1-) linkage at the non-reducing termini of sugar compounds and provides a reagent for use in hydrolysis by said method.

2. Description of Related Art

Oligosaccharides of glycoproteins and glycosphingolipids change in various biological events, including cancer and cell differentiation. To elucidate the biological functions and structures of these oligosaccharides, exoglycosidases are useful. Various exoglycosidases have been isolated from a number of prokaryotic and eukaryotic sources. However, no enzyme hydrolyzes hetero-oligosaccharides to release disaccharide.

Gal-GlcNAc structures are often found at the non-reducing termini of oligosaccharides. These oligosaccharide structures have been divided into two groups: type 1, with Gal$\beta$1-3GlcNAc$\beta$1-, and type 2, with Gal$\beta$1-4GlcNAc$\beta$1-. The N-acetyllactosamine type of sugar chain from several glycoproteins also has type 1 structure (Mizuochi et al., *J. Biol. Chem.* 254, 6419, 1979; Mizuochi et al., *J. Biol. Chem.* 255, 3526, 1980; Takasaki & Kobata, *Biochemistry* 25, 5709, 1986; Townsend et al., *Biochemistry* 25, 5716, 1986). NMR, mass spectrometry, and methylation analysis have been used to distinguish type 1 and type 2 structures, but much oligosaccharide is needed for the analysis. Another analytical method is $\beta$-galactosidase digestion, which requires little oligosaccharide. Diplococcal $\beta$-galactosidase specifically cleaves $\beta$1-4 galactosyl linkages but not $\beta$1-3 or $\beta$1-6 galactosyl linkages (Paulson et al., *J. Biol. Chem.* 253, 5617, 1978). Thus, oligosaccharides hydrolyzed by this enzyme have a type 2 structure, and oligosaccharides not hydrolyzed by this enzyme do not have a type 2 structure. Type 1 structure cannot be identified directly with this enzyme.

SUMMARY OF THE INVENTION

The object of this invention is to provide a method for the hydrolysis of only the lacto-N-biosidic linkage at the non-reducing termini of sugar compounds and to provide a reagent for use in hydrolysis by said method.

In summary, one aspect of this invention relates to a method for the specific hydrolysis of a sugar compound represented by formula I:

  (I)

wherein R represents a sugar residue, only at the lacto-N-biosidic linkage, characterized by the use of a glycosidase that is specific for only the lacto-N-biosidic linkage in said sugar compound.

Another aspect of this invention relates to a reagent for use in the specific hydrolysis of a sugar compound represented by formula I:

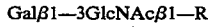  (I)

wherein R represents a sugar residue, only at the lacto-N-biosidic linkage, which comprises an enzymatically effective amount of a glycosidase that is specific for only the lacto-N-biosidic linkage in said sugar compound represented by formula I, in a suitable medium.

The sugar compound represented by formula I of this invention includes sugar compounds containing lacto-N-biose structures at the non-reducing termini. The sugar residue represented by R includes monosaccharides, oligosaccharides, polysaccharides, oligosaccharides of glycolipids or glycoproteins, and the like.

The inventors of this invention achieved the purpose of this invention during research into enzymes that cleave lacto-N-biosidic linkages by discovery of a strain of Streptomyces that produces an exoglycosidase specific for lacto-N-biosidic linkages. This exoglycosidase is named lacto-N-biosidase. The invention is based on research into methods to produce this enzyme, the properties of the enzyme, and methods for its use. Below, this invention is described in detail.

Method for the Preparation of the Enzyme

The microbial strain used to produce the enzyme of this invention can be any strain that can produce lacto-N-biosidase, or a mutant of such a strain. One example of a microbial strain that can produce lacto-N-biosidase is Streptomyces sp 142, which has been deposited at the Fermentation Research Institute, Agency of Industrial Science and Technology1-3, Higushi 1-3 chome Tsukuba-shi Ibaraki Ken 305, Japan, as FERM P-10806. the properties of this strain were disclosed in Japan Patent Application No. 89-234791.

The lacto-N-biosidase of this invention can be obtained, for example, by isolation from the culture broth of, for example, the strain named above. The method used for cultivation of the strain can be the usual method used for the cultivation of microorganisms.

Any nutrient that the strain being used can assimilate to produce lacto-N-biosidase may be added to the culture medium. Mucin, fucose, lactose, maltose, glucose, glycerol, galactose, and the like may be used as carbon sources, and peptone, bouillon, yeast extract, corn steep liquor, and the like may be used as nitrogen sources. In addition, minerals and metal salts, such as phosphates, potassium salts, and magnesium salts, may be added.

The yield of lacto-N-biosidase varies depending on the culture conditions. As a rule, culture is for preference at a temperature in the range from 20° to 35° C. and at a pH in the range from 5 to 8; and good production can be achieved by culture with aeration and agitation for one to seven days. The optimum culture conditions can be selected depending on the strain used and the composition of the culture medium.

Lacto-N-biosidase produced by the method of this invention is accumulated inside or secreted outside the microbial cells depending on the strain used and the composition of the culture medium. Cells can be isolated from the culture broth by, for example, centrifugation. The enzyme produced can be isolated and purified by use of known techniques usually used for glycosidases. For example, collected microbial cells can be dispersed in a buffer and then disrupted by ultrasonic treatment to allow extraction of the enzyme. After removal of the residue by centrifugation, ammonium sulfate can be added to the extract for salting out. The precipitate that separates out can be dissolved in a buffer, and the solution can be dialyzed against the same buffer. The dialyzate can then be purified by affinity chromatography, hydrophobic chromatography, ion-exchange chromatography, or molecular-sieve chromatography, thus giving the lacto-N-biosidase of this invention.

Lacto-N-biosidase assay

Lacto-N-biosidase was assayed by being incubated for 20 min with the compound described by formula II below at the concentration of 2 μM at 37° C. in 10 μl of 100 mM potassium phosphate buffer, pH 6.0.

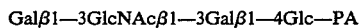

Galβ1—3GlcNAcβ1—3Galβ1—4Glc—PA     (II)

wherein PA represents a pyridylamino residue. Oligosaccharides labeled with 2-aminopyridine can be obtained by the method described in U.S. Pat. No. 4,975,533. Then 40 μl of 1% trifluoroacetic acid was added to the reaction mixture to stop the reaction. A portion containing 10 pmol of PA-oligosaccharides was then analyzed by HPLC with an amino-silica column (Palpak Type N column, 4.6×250 mm, Takara Shuzo), and detected by fluorescence with the excitation and emission wavelengths of 310 and 380 nm, respectively. Elution was at the flow rate of 1.0 ml/min at 40° C. with a 70:30 (v/v) mixture of acetonitrile and 0.2M triethylamine acetate buffer, pH 7.3. The degree of hydrolysis was calculated from the peak areas of the substrate and the product, PA-lactose, in comparison with the peak area of the corresponding standard PA-oligosaccharide. One unit of activity was defined as the amount of enzyme needed to release 1 μmol of PA-lactose per minute under the conditions described above.

Action and Substrate Specificity

This enzyme is specific for lacto-N-biosidic linkages in sugar compounds. The enzyme specifically hydrolyzes sugar compounds containing a type 1 structure at the non-reducing termini to produce lacto-N-biose. Substrate specificity studies with oligosaccharides labelled with 2-aminopyridine showed that the enzyme specifically hydrolyzed lacto-N-tetraose (Galβ1-3GlcNAcβ1-3Galβ1-4Glc) but did not hydrolyze lacto-N-neotetraose (Galβ1-4GlcNAcβ1-3Galβ1-4Glc), lacto-N-triose, lacto-N-fucopentaose I, asialo G$_{M1}$ tetrasaccharide, sialyl lacto-N-tetraose, or poly-N-acetyllactosamine. Structural analysis of enzyme digests of the N-acetyllactosamine type of triantennary sugar chain with a type 1 structure (the compound described by formula III below) showed that lacto-N-biose and the N-acetyllactosamine type of biantennary sugar chain (the compound described by formula IV below) were produced.

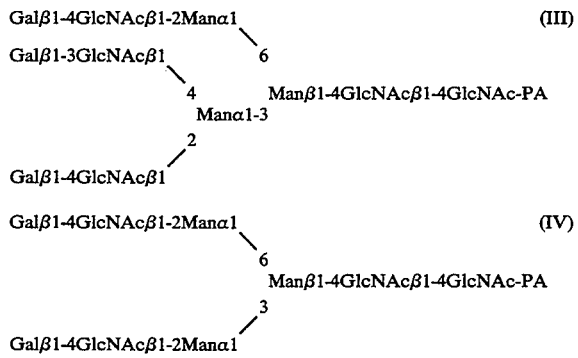

wherein PA represents a pyridylamino residue. This enzyme hydrolyzes the compound described by formula V to produce lacto-N-biose and p-nitrophenol.

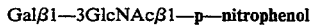

Galβ1—3GlcNAcβ1—p—nitrophenol     (V)

Physicochemical Properties

The lacto-N-biosidase of this invention has the physicochemical properties described below.

1. Effects of pH on enzyme activity and stability

The enzyme activity was maximum at pH 5.5–6.0 (FIG. 1), and the enzyme was stable in the pH range of 4.0–7.0 when kept at 4° C. for 16 h (FIG. 2).

3. Effect of temperature on enzyme activity.

The enzyme activity was maximum at 40°–55° C. (FIG. 3).

4. Molecular weight

The molecular weight of lacto-N-biosidase was approximately 29,000 when estimated by gel filtration with TSKgel HW55S.

The method and the reagent of this invention can be used in studies done to identify type 1 structures in glycoconjugates, to distinguish type 1 oligosaccharides from type 2 oligosaccharides, and to elucidate the functions of lacto-N-biosyl residues in glycoconjugates. In particular, with its use, the Le$^a$ structure can be easily distinguished from the Le$^x$ structure by use of lacto-N-biosidase and α-1,¾ fucosidase (Ogata-Arakawa et al., Arch. Biochem. Biophys. 181, 353, 1977; Scudder et al., J. Biol. Chem. 265, 16472, 1990; Sano et al., J. Biol. Chem. 267, 1522, 1992). PA-lactose was obtained when PA-lacto-N-fucopentaose II (Le$^a$ pentasaccharide) was treated with a mixture of lacto-N-biosidase and α-1,¾ fucosidase, and PA-lacto-N-neotetraose was obtained when PA-lacto-N-fucopentaose III (Le$^x$ pentasaccharide) was treated with the mixture of the two enzymes.

Figure 1:
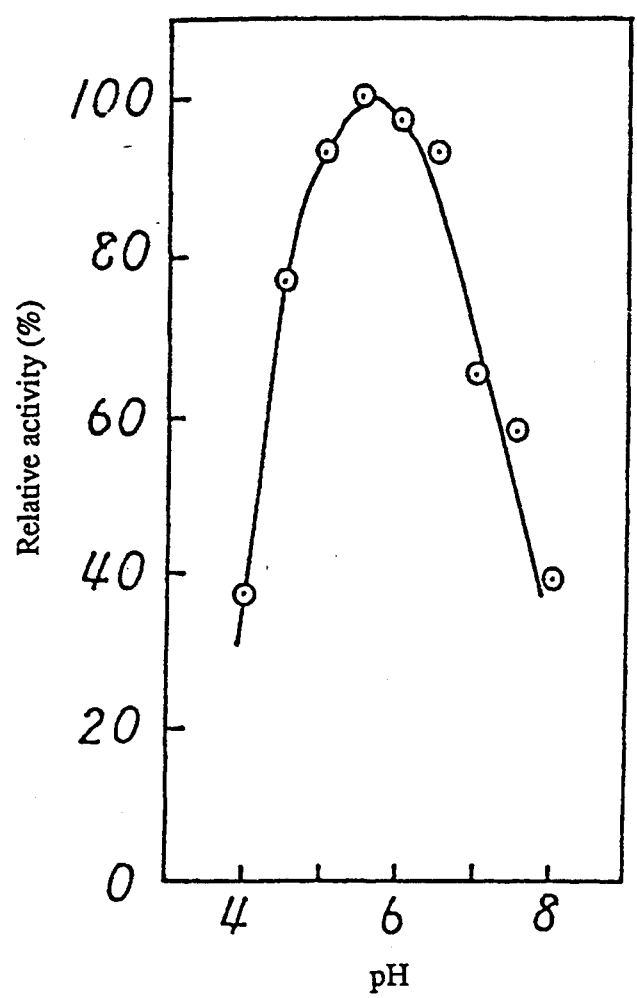
FIG. 1 shows the effects of pH on the enzyme activity.
Figure 2:
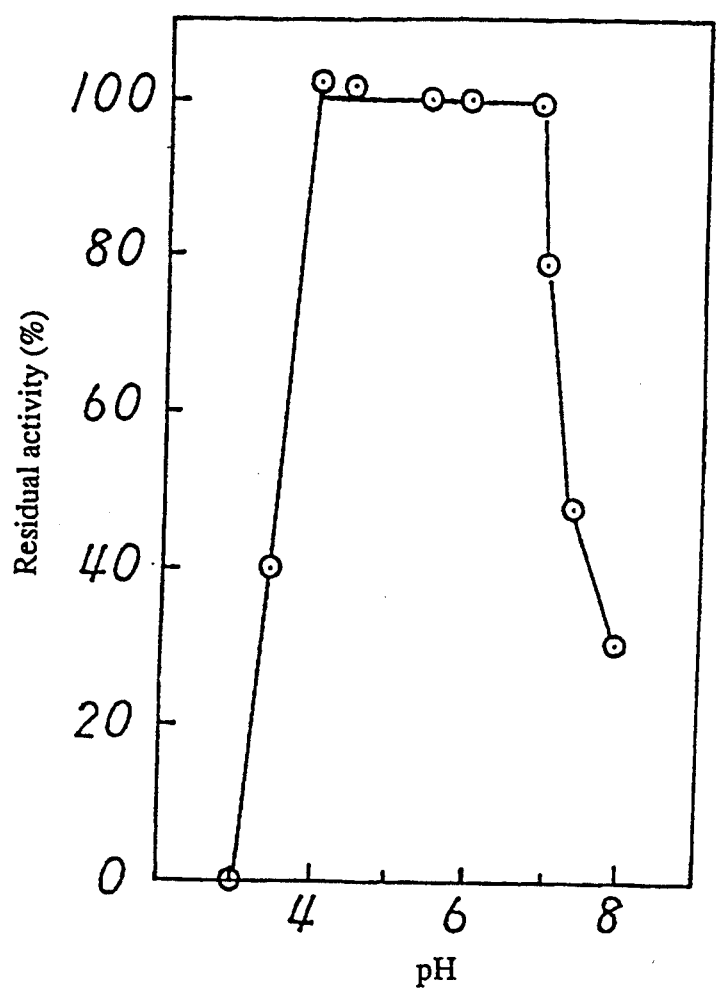
FIG. 2 shows the effects of pH on the enzyme stability. The enzyme was treated in 500 mM buffers of different pHs at 4° C. for 16 h, and the remaining activity was assayed under the conditions described above.
Figure 3:
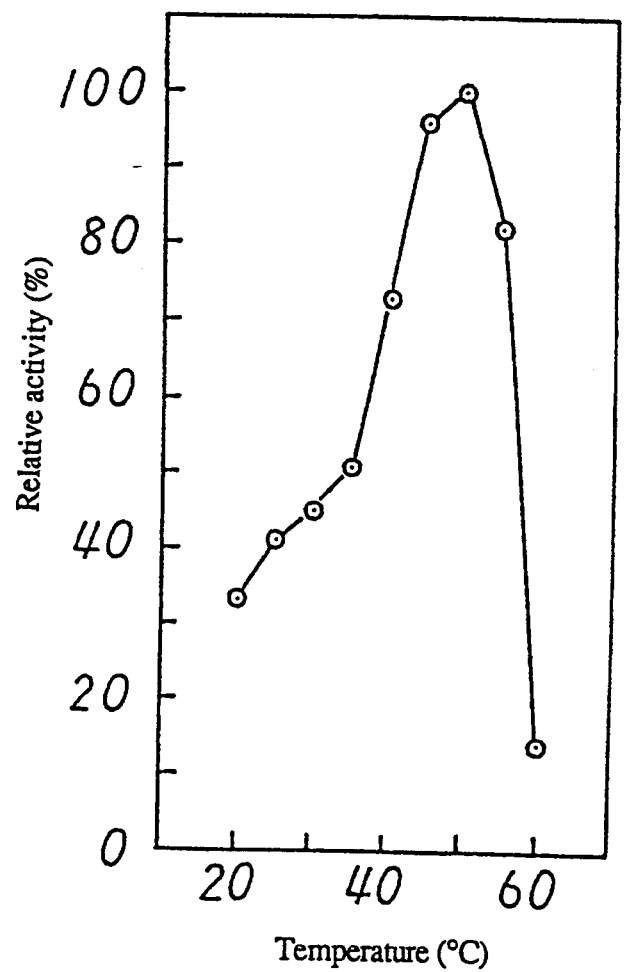
FIG. 3 shows the effects of temperature on the enzyme activity.

The following example is given to illustrate this invention but is not intended to limit its scope.

EXAMPLE 1

Streptomyces sp 142 (FERM P-10806), isolated from a soil sample, produced lacto-N-biosidase when grown on a medium containing L-fucose as the sole carbon source as described below. Spores and mycelia of the strain grown on an agar slant were used to inoculate 100 ml of a medium containing 1% L-fucose, 0.3% peptone, 0.05% yeast extract, 0.1% KH$_2$PO$_4$, and 0.05% MgSO$_4$.7H$_2$O (pH 7.0) in a 500-ml flask. Culture was for 40 h at 27° C. with vigorous rotary shaking and then 25 ml of broth was transferred to a 2-liter flask containing 500 ml of the same medium. Culture was continued for 48 h at 27° C. with vigorous rotary shaking.

Unless otherwise stated, all purification steps were done at 4° C.

The cells were harvested from 500 ml of culture broth by centrifugation at 12,000×g for 20 min and washed with 100 ml of 10 mM potassium phosphate buffer, pH 7.0, containing 10 mM EDTA, 1 mM o-phenanthroline, and 1 mM phenylmethylsulfonyl fluoride (PMSF) (buffer A). The cells were resuspended in 100 ml of buffer A and sonicated (Kubota Insonator Model 200M) at 9 kHz for 15 min; the cell-free extract was obtained by centrifugation at 12,000×g for 20 min, and dialyzed against 20 volumes of buffer A.

The dialyzed cell-free extract was put on a column (4.0×23 cm) of DEAE-Sepharose CL-6B equilibrated with 50 mM potassium phosphate buffer, pH 6.0, containing 10 mM EDTA, 1 mM o-phenanthroline, and 1 mM PMSF (buffer B). The column was washed with 3 bed volumes of buffer B. Fractions that eluted with buffer B contained lacto-N-biosidase and were pooled and concentrated to 30 ml with an Advantec ultrafiltration cell with a P0200 ultrafilter. Ammonium sulfate was added to the concentrated enzyme solution. The enzyme solution was put on a column (1.0×6.0 cm) of phenyl-Sepharose CL-4B equilibrated with buffer B containing 1.5M ammonium sulfate and eluted at the flow rate of 60 ml/h by being washed with 3 bed volumes of buffer B containing 1.5M ammonium sulfate followed by buffer B (fraction size, 2 ml). Fractions with enzyme activity were pooled and concentrated to 1 ml. The concentrated enzyme solution was put on a TSKgel HW55S column (1.5×90 cm) equilibrated with 50 mM potassium phosphate buffer, pH 6.0, containing 100 mM NaCl, 0.01% NaN$_3$, and 0.1% Brij 58. The enzyme was eluted with the same buffer (fraction size, 2 ml), and fractions with enzyme activity were pooled. Lacto-N-biosidase prepared with TSKgel HW55S was assayed for α-fucosidase, α-mannosidase, α-galactosidase, β-galactosidase, and β-N-acetylglucosaminidase activities toward synthetic p-nitrophenyl glycoside substrates, but such activties were not found.

EXAMPLE 2

Streptomyces sp 142 (FERM P-10806) produced lacto-N-biosidase when grown on a medium containing mucin as the sole carbon source as described below. Spores and mycelia of the strain grown on an agar slant were used to inoculate 100 ml of a medium containing 1% porcine gastric mucin, 0.3% peptone, 0.01% yeast extract, 0.1% KH$_2$PO$_4$, and 0.05% MgSC$_4$ 7 H$_2$O (pH 7.0) in a 500-ml flask. Culture was for 40 h at 27° C. with vigorous rotary shaking and then 25 ml of broth was transferred to a 2-liter flask containing 500 ml of the same medium. Culture was continued for 48 h at 27° C. with vigorous rotary shaking.

Unless otherwise stated, all purification steps were done at 4° C.

The culture broth was centrifuged at 12,000× g for 20 min to remove the cells. The supernatant obtained (500 ml) was dialyzed against 20 volumes of 20 mM potassium phosphate buffer, pH 7.5, containing 0.1% Brij 58, 0.1% 2-mercaptoethanol, and 0.5 mM PMSF.

The dialyzed crude enzyme solution was put on a column (2.5×15 cm) of Q-Sepharose equilibrated with 50 mM potassium phosphate buffer, pH 7.5, containing 0.1% Brij 58, 0.1% 2-mercaptoethanol, and 0.5 mM PMSF (buffer C). The column was washed with 3 bed volumes of buffer C. Fractions containing lacto-N-biosidase that eluted with buffer C were pooled and dialyzed against 50 mM sodium acetate buffer, pH 5.5, containing 0.1% Brij 58, 0.1% 2-mercaptoethanol, and 0.5 mM PMSF (buffer D). The dialyzed enzyme solution was put on a column (1.0×6.0 cm) of phenyl-Sepharose CL-4B equilibrated with buffer B containing 1.5M ammonium sulfate and eluted at the flow rate of 60 ml/h by being washed with 3 bed volumes of buffer B containing 1.5M ammonium sulfate followed by buffer B (fraction size, 2 ml). Fractions with enzyme activity were pooled and concentrated to 1 ml. The concentrated enzyme solution was put on a TSKgel HW55S column (1.5×90 cm) equilibrated with 50 mM potassium phosphate buffer, pH 6.0, containing 100 mM NaCl, 0.01% NaN$_3$, and 0.1% Brij 58. The enzyme was eluted with the same buffer (fraction size, 2 ml), and fractions with enzyme activity were pooled. Lacto-N-biosidase prepared with TSKgel HW55S was assayed for α-fucosidase, α-mannosidase, α-galactosidase, β-galactosidase, and β-N-acetylglucosaminidase activities toward synthetic p-nitrophenyl glycoside substrates, but such activities were not found.

EXAMPLE 3

To elucidate the reaction products of lacto-N-biosidase obtained by the method of example 1, the structures of the enzyme reaction products were analyzed in detail with the PA-oligosaccharide shown as formula VI below as the substrate. PA-oligosaccharide described by formula VI (about 100 nmol; Takara Shuzo Co.) mixed with lacto-N-biosidase (total, 0.6 mU) prepared as described in example 1 was digested for 60 h at 37° C. in a final volume of 360 μl containing 0.1M potassium phosphate buffer, pH 6.0. The reaction mixture was pyridylaminated by the method described in U.S. Pat. No. 4,975,533 and analyzed by HPLC with an amino-silica column. There were two peaks of PA-oligosaccharides: fractions 1 and 2. The elution position of fraction 1 was the same as that of the PA-oligosaccharide described by formula VII, and the elution position of fraction 2 was the same as that of PA-oligosaccharide described by formula VIII below. The amounts of these two products, calculated from the peak areas of fractions 1 and 2, were identical to that of the PA-oligosaccharide substrate of formula VI. These results and the structural analysis of the reaction products by mass spectrometry and $^1$H NMR showed that the two oligosaccharides described by formula VIII and IX were produced from the PA-oligosaccharide of formula VI, and that the only lacto-N-biosidic linkage in the substrate was cleaved by the enzyme reaction.

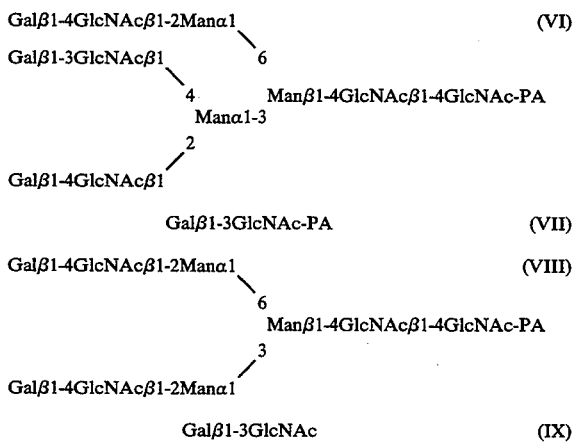

wherein PA represents a pyridylamino residue.

As described in detail above, this invention provides a method for the hydrolysis of only the lacto-N-biosidic linkage at the non-reducing termini of sugar compounds and to provide a reagent for use in hydrolysis by said method. This invention can be used in procedures indispensable to the structural and functional analysis of glycoconjugates.

What we claim is:

1. An isolated and purified lacto-N-biosidase having the following properties:

(1) action: hydrolyzes an oligosaccharide of formula (i) specifically at the arrow-marked site:

   Galβ1-3GlcNAcβ1-R (i)

wherein R represents a sugar residue which is optionally labeled with fluorescent label at the reducing end;

(2) substrate specificity: hydrolyzes a sugar compound of formula (ii) specifically at the arrow-marked site:

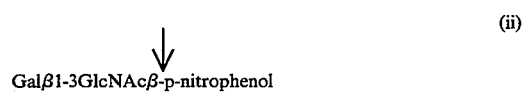
   Galβ1-3GlcNAcβ-p-nitrophenol (ii)

but does not hydrolyze an oligosaccharide described by formula (iii):

   Galβ1—4GlcNAcβ1—R' (iii)

wherein R' represents a sugar residue which is optionally labeled with fluorescent label at the reducing end;

(3) optimal pH: 5.5–6.0;
   (4) pH stability: stable in the pH range of 4.0–7.0 when kept at 4° C. for 16 hours; and
   (5) optimal temperature: 40° C.–55° C.;
   (6) obtained from Streptomyces sp 142.

2. A method for the hydrolysis of an oligosaccharide of formula (i) specifically at the arrow-marked site:

   Galβ1-3GlcNAcβ1-R (i)

wherein R represents a sugar residue which is optionally labeled with fluorescent label at the reducing end; which comprises contacting said oligosaccharide with an isolated glycosidase of claim 1.

* * * * *